Figure 1:
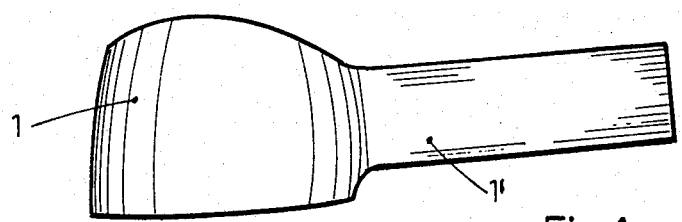

United States Patent [19]

von Weissenfluh

[11] Patent Number: 4,824,365
[45] Date of Patent: Apr. 25, 1989

[54] DENTAL MATRIX IN A FLEXIBLE STRIP WITH TIGHTENER CONNECTED TO IT

[75] Inventor: Hans von Weissenfluh, Magadino, Switzerland

[73] Assignee: Hawe-Neos Dental Dr. H. Von Weissenfluh S.A., Gentilino, Switzerland

[21] Appl. No.: 156,144

[22] Filed: Feb. 16, 1988

[30] Foreign Application Priority Data

May 14, 1987 [CH] Switzerland .......................... 1845/87

[51] Int. Cl.⁴ .................................................. A61C 9/00
[52] U.S. Cl. ......................................... 433/40; 433/39
[58] Field of Search .............................. 433/39, 40, 41

[56] References Cited

U.S. PATENT DOCUMENTS

| | | | |
|---|---|---|---|
| 983,844 | 2/1911 | Shannon | 433/39 |
| 3,383,769 | 5/1968 | Davis | 433/39 |

Primary Examiner—Robert Peshock
Attorney, Agent, or Firm—Young & Thompson

[57] ABSTRACT

The matrix consisting of a thin flexible strip of plastic comprises a loop 1 to be placed around the tooth to give the desired shape to the filling material. It is permanently connected to an annular tightener (2) made of material permanently deformable by pressure with the fingers and dentist's forceps, for example, of annealed aluminum sheet. It exhibits, in the front, a slit (3) through which pass the two terminal extensions (1',1") of flexible strip (1) and, in the back, tabs (2',2") between which are permanently fastened the ends of said terminal extensions (1, 1") of said strip, so that by compressing said annular tightener (arrows 4, 5) it determines the slipping of slit (3) like a slider on the extensions (1', 11") of the strip, the narrowing of loop (1) and the perfect adherence of the loop of the strip to the tooth.

8 Claims, 1 Drawing Sheet

U.S. Patent

Apr. 25, 1989

4,824,365

DENTAL MATRIX IN A FLEXIBLE STRIP WITH TIGHTENER CONNECTED TO IT

Matrices in a flexible strip, for example of plastic, to be placed around the tooth during filling to give the filling material the desired shape, are known.

Tighteners are also known which are suitable for holding said strip against the tooth to avoid slipping during filling.

Said known tighteners are very complex and bulky and involve a considerable loss of time for their application to the strip for each filling.

According to the invention, the tightener is connected to the strip so as not to involve any loss of time by the dentist for each filling and is so simple, effective and inexpensive as to achieve a real advance relative to the known art, for example, relative to the tightener according to U.S. Pat. No. 3,383,769 which is bulky and does not give any guarantee of holding the matrix against the tooth during filling.

The matrix under discussion here is characterized by an annular tightener connected to the loop-shaped strip, a tightener made of material permanently deformable by pressure of the fingers or dentist's forceps and exhibiting, in the front, a slit through which pass the two terminal extensions of the flexible strip and, in the back, tabs between which are permanently fastened the ends of said terminal extensions of said strip, so that by compressing said annular tightener it determines the slipping of the slit like a slider on the extensions of the strip and the perfect adherence of the loop of the strip to the tooth, said tabs then being bent to occupy the minimum space while preventing contact with the cheek.

According to a preferred embodiment, the annular tightener exhibits, above and below the slit, a projection so that the two projections assure the perfect adherence of the matrix to the tooth, avoiding slipping.

The accompanying drawing represents said preferred embodiment of the invention in a nonlimiting and nonbinding way.

FIG. 1 represents the lateral view of only the strip constituting the matrix.

Figure 2:
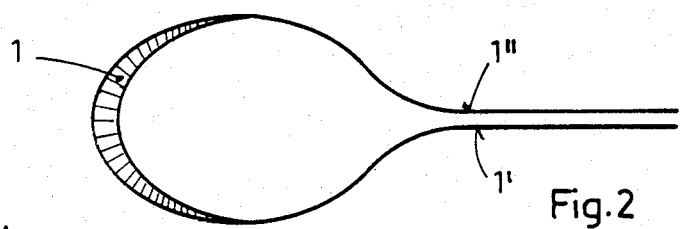

FIG. 2 the top plan view of the strip of FIG. 1.

Figure 3:
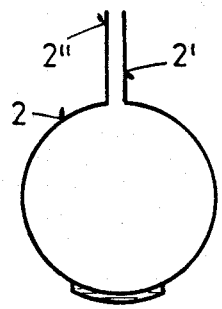

FIG. 3 the top plan view of only the tightener.

Figure 4:
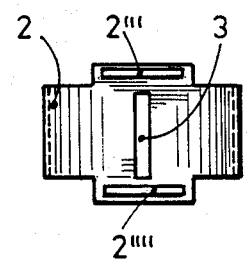

FIG. 4 the front view of the tightener of FIG. 3.

Figure 5:
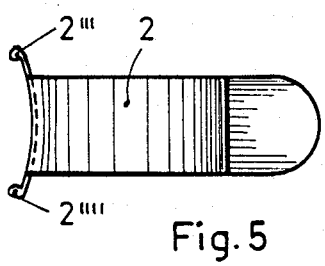

FIG. 5 the side view of the tightener of FIG. 3.

Figure 6:
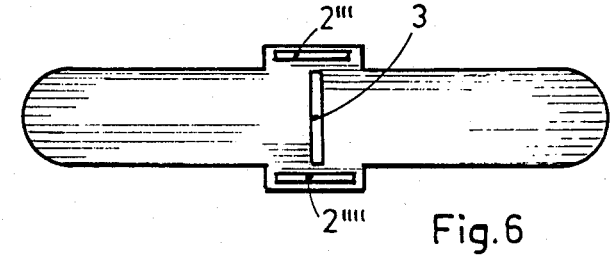

FIG. 6 the development in a plane of only the tightener.

Figure 7:
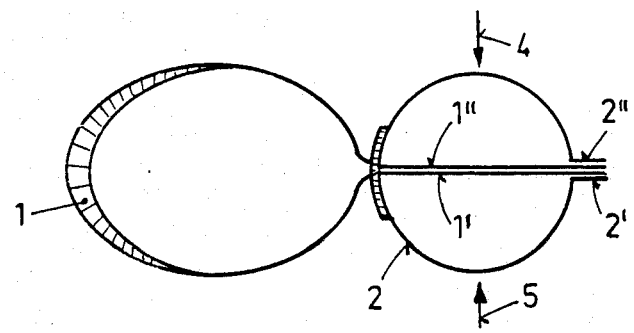

FIG. 7 the unit of the matrix and tightener.

With reference to FIGS. 1 and 2: the matrix, made up of a strip of thin plastic, is shaped in a loop 1 to surround the tooth during filling and ends in two extensions 1' and 1".

To strip 1, 1', 1" is permanently applied tightener 2 (FIGS. 3, 4, 5, 6) made, for example of thin annealed aluminum sheet to be able to be easily and permanently deformed if pressed with the fingers or the dentist's forceps in the direction of arrows 4 and 5 (FIG. 7).

For this purpose, the two extensions 1', 1" of the strip are made to go through slit 3 (FIG. 4) of tightener 2 and fastened at their ends to tabs 2', 2" of tightener 2, for example, by means of heat-setting and then bending of the tabs to avoid injuring the cheek.

Projections 2''', 2'''', obtained, for example, by drawing, serve to assure the perfect adherence of loop 1 of the matrix of the tooth, avoiding slipping.

It is clear that the ends of extensions 1', 1" of the strip being fastened in 2', 2" (FIG. 7), by pressing the tightener according to arrows 4, 5 to go from a circular shape to an elliptic shape, slit 3 slips like a slider on extensions 1', 1" forcing loop 1 to become smaller and fit the tooth perfectly so as to give the filling material the desired perfect shape.

Tightener 2 being permanently and not elastically deformed, the return of loop 1 to the enlarged shape is impossible.

The cost of the tightener in question is negligible in comparison with the advantages that flow from it.

It is provided that the shape of the strip and of the tightener in question and the nature of the material that constitutes them can, however, vary without going outside the scope of protection of the patent.

I claim:

1. A dental matrix band and tightener assembly comprising:
   a loop-shaped dental matrix band including two terminal extensions each having respective juxtaposed end portions;
   a loop-shaped tightener for said dental matrix band having opposing deformable portions of said loop, said lightener being in the form of single strip having a central portion and two terminal extensions extending from said central portion each having respective end portions, said central portion of said tightener including an opening which slidably receives both said terminal extensions of said matrix band, and said respective end portions of said terminal extensions of said tightener extending along each side of said juxtaposed end portions of said matrix band and being fastened to said end portions of said matrix band to form said opposing deformable portions of said loop.

2. The dental matrix band and tightener assembly of claim 4 wherein said respective end portions of said matrix band and said tightener are fastened together by heat sealing.

3. The dental matrix band and tightener assembly of claim 1 wherein said tightener is comprised of a material which may be permanently deformed by application of pressure to the the loop portion of said tightener.

4. The dental matrix band and tightener assembly of claim 1 wherein said opening in said central portion of said tightener is in the form of a slit.

5. The dental matrix band and tightener assembly of claim 6 wherein said tightener is comprised of aluminum.

6. The dental matrix band and tightener assembly of claim 1 wherein said terminal extensions of said matrix band and said tightener are each in the form of thin strips.

7. The dental matrix band and tightener assembly of claim 1 wherein said matrix band is comprised of a plastic material.

8. The dental matrix band and tightener assembly of claim 1 further including two lateral projections extending from said central portion of said tightener toward said loop of said matrix band.

* * * * *